(12) United States Patent
Nomura et al.

(10) Patent No.: US 11,207,245 B2
(45) Date of Patent: Dec. 28, 2021

(54) COMPOSITE FOR DENTAL PATTERN RESIN

(71) Applicant: GC CORPORATION, Shizuoka (JP)

(72) Inventors: Yoshie Nomura, Kasugai (JP); Kenji Kojima, Kasugai (JP); Tatsuya Fujimoto, Kasugai (JP)

(73) Assignee: GC CORPORATION, Shizuoka (JP)

( * ) Notice: Subject to any disclaimer, the term of this patent is extended or adjusted under 35 U.S.C. 154(b) by 17 days.

(21) Appl. No.: 16/566,109

(22) Filed: Sep. 10, 2019

(65) Prior Publication Data
US 2020/0093708 A1 Mar. 26, 2020

(30) Foreign Application Priority Data
Sep. 26, 2018 (JP) .............................. JP2018-179914

(51) Int. Cl.
A61K 6/887 (2020.01)
C08F 220/18 (2006.01)
C08F 220/28 (2006.01)
C08K 5/18 (2006.01)

(52) U.S. Cl.
CPC ............ A61K 6/887 (2020.01); C08F 220/18 (2013.01); C08F 220/28 (2013.01); C08F 220/282 (2020.02); C08K 5/18 (2013.01)

(58) Field of Classification Search
CPC ..................................................... A61K 6/887
See application file for complete search history.

(56) References Cited

U.S. PATENT DOCUMENTS

| 4,913,939 A * | 4/1990 | Montgomery | A61K 8/37 427/389 |
| 5,663,214 A * | 9/1997 | Okada | A61K 6/887 523/120 |
| 2009/0025638 A1* | 1/2009 | Inoue | B29C 64/165 118/712 |

FOREIGN PATENT DOCUMENTS

JP 2007-051116 A 3/2007

* cited by examiner

Primary Examiner — Michael F Pepitone
(74) Attorney, Agent, or Firm — Sughrue Mion, PLLC

(57) ABSTRACT

To provide a composite for a dental pattern resin whose shrinkage when curing and expansion when heated can be both suppressed as its usability is kept, the composite for a dental pattern resin includes a liquid formulation and a powder formulation, wherein the liquid formulation includes a polymerizable monofunctional (meth)acrylate, a polymerizable polyfunctional (meth)acrylate, and a polymerization accelerator, and the powder formulation includes more than 5 mass % of a (meth)acrylate copolymer on the basis of the total powder formulation.

10 Claims, No Drawings

COMPOSITE FOR DENTAL PATTERN RESIN

CROSS-REFERENCE TO RELATED APPLICATIONS

This application claims priority under U.S.C. § 119(a) to Japanese Patent Application No. 2018-179914 filed on Sep. 26, 2018.

TECHNICAL FIELD

The present invention relates to a composite for a dental pattern resin used for dental precision casting.

BACKGROUND ART

A material for a dental pattern is a material for making a wax pattern used in a so-called lost-wax process, and is a material burned out after invested in an investment (refractory material) as a model for dental precision casting. Metal or resin is filled with a space formed by this burning. A chemically polymerizable resin into which wax or a (meth) acrylate polymer is incorporated as filler has been conventionally used as such a material for a dental pattern. A chemically polymerizable resin has, however, the disadvantages of deformation when handled, and bad usability.

In recent years, materials for a dental pattern (composites for a dental pattern resin) comprising a powder component and a liquid component have been provided as, for example, JP 2007-51116 A. According to this, problems as described above can be solved because a powder component and a liquid component are used.

SUMMARY OF INVENTION

Technical Problem

A conventional composite for a dental pattern resin as described above has the following problems: the composite deforms or is difficult to be removed from a model because of its large shrinkage when curing; and an investment (refractory material) is destroyed or cracks because the composite hugely expands when heated for burning.

It is a precondition for solving these problems however that usability of the composite shall be kept when the composite is molded.

An object of the present invention is to provide a composite for a dental pattern resin whose shrinkage when curing and expansion when heated can be both suppressed as its usability is kept.

Solution to Problem

An aspect of the present invention is a composite for a dental pattern resin comprising a liquid formulation and a powder formulation, wherein the liquid formulation comprises a polymerizable monofunctional (meth)acrylate, a polymerizable polyfunctional (meth)acrylate, and a polymerization accelerator, and the powder formulation comprises more than 5 mass % of a (meth)acrylate copolymer on the basis of the total powder formulation.

The content of the polyfunctional (meth)acrylate may be 2 mass % to 30 mass % on the basis of the total liquid formulation.

The polyfunctional (meth)acrylate may be at least one of ethylene glycol di(meth)acrylate and trimethylolpropane tri (meth)acrylate.

The content of the polymerization accelerator may be 3 mass % to 10 mass % on the basis of the total liquid formulation. The polymerization accelerator may be N,N'-dimethyl-p-toluidine.

The content of the (meth)acrylate copolymer may be more than 5 mass % and no more than 98 mass % on the basis of the total powder formulation. The volume median particle size of the (meth)acrylate copolymer may be 40 µm to 130 µm.

The (meth)acrylate copolymer may comprise ethyl (meth) acrylate and methyl (meth)acrylate. At this time, the content of the ethyl (meth)acrylate in the (meth)acrylate copolymer may be 20 mass % to 90 mass %, and the content of the methyl (meth)acrylate in the (meth)acrylate copolymer may be 10 mass % to 80 mass %.

The powder formulation may further comprise a flowability-improving agent. At this time, the content of the flowability-improving agent may be 0.1 mass % to 20 mass % on the basis of the total powder formulation. The flowability-improving agent may be polymethyl (meth)acrylate. The volume median particle size of the flowability-improving agent may be 0.05 µm to 20 µm.

Advantageous Effects of Invention

Shrinkage of the composite for a dental pattern resin of the present invention when the composite cures and expansion thereof when the composite is heated can be both suppressed as usability thereof is kept.

DESCRIPTION OF EMBODIMENTS

Embodiments of the present invention will be described. A composite for a dental pattern resin according to one embodiment of the present invention, having a liquid formulation and a powder formulation, is formed by mixing the liquid formulation and the powder formulation. Hereinafter each of the liquid formulation and the powder formulation will be described. Hereinafter "(meth)acrylate" means acrylate and/or methacrylate.

[Liquid Formulation]

<Monofunctional (Meth)Acrylate Monomer>

The liquid formulation in the composite for a dental pattern resin includes a monofunctional (meth)acrylate monomer having one polymerizable functional group of a carbon-carbon double bond (monofunctional structure), which is preferably a radical-polymerizable monofunctional (meth)acrylate monomer.

The content of the monofunctional (meth)acrylate monomer in the liquid formulation in the composite for a dental pattern resin is preferably 65 mass % to 97 mass %. Containing the monofunctional (meth)acrylate monomer as the major component (more than 50 mass %) as described above makes it possible to suppress a temperature rise when the composite is polymerization-cured, to avoid the problem of a burn and air bubbles mixing during operation, and to prevent usability from deteriorating. The content thereof is more preferably no less than 75 mass %. When the content of the monofunctional (meth)acrylate monomer is more than 97 mass %, the composite for a dental pattern resin hugely expands due to heating when burned, which may lead to destruction of, and cracks in an investment (refractory material).

Any monofunctional (meth)acrylate monomer may be employed. One monofunctional (meth)acrylate monomer may be used alone, and a plurality of monofunctional (meth)acrylate monomers may be used in combination.

Specific examples of a material thereof include methyl (meth)acrylate, isobutyl (meth)acrylate, benzyl (meth)acrylate, lauryl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerin mono(meth)acrylate, erythritol mono(meth)acrylate, N-methylol (meth)acrylamide, N-hydroxyethyl (meth)acrylamide, N-(dihydroxyethyl) (meth)acrylamide, (meth)acryloyl oxydodecylpyridinium bromide, (meth)acryloyl oxydodecylpyridinium chloride, (meth)acryloyl oxyhexadecylpyridinium chloride, (meth)acryloyl oxydecylammonium chloride, ethyl (meth)acrylate, isopropyl (meth)acrylate, 3-hydroxypropyl (meth)acrylate, 2-hydroxy-1,3-dimethacryloxypropane, t-butyl (meth)acrylate, n-butyl (meth)acrylate, isobutyl (meth)acrylate, butoxyethyl (meth)acrylate, glycidyl (meth)acrylate, 2-methoxyethyl (meth)acrylate, 2-hexylethyl (meth)acrylate, benzil (meth)acrylate, and ethylene glycol (meth)acrylate.

Among them, a methyl (meth)acrylate monomer is preferably employed as the monofunctional (meth)acrylate monomer. According to this, air bubbles are hard to form, and good usability is achieved more certainly.

<Polyfunctional (Meth)Acrylate Monomer>

The liquid formulation in the composite for a dental pattern resin includes a polyfunctional (meth)acrylate monomer having at least two polymerizable functional groups of a carbon-carbon double bond (polyfunctional structure), which is preferably a radical-polymerizable polyfunctional (meth)acrylate monomer.

The content of the polyfunctional (meth)acrylate monomer in the liquid formulation in the composite for a dental pattern resin is preferably 2 mass % to 30 mass %. This makes it possible to suppress expansion of the composite for a dental pattern resin when the composite is burned to be heated, and to prevent an investment (refractory material) from being destroyed and cracking. This is imagined to be because a cross-linked structure is formed by polymerization of the polyfunctional (meth)acrylate monomers, which suppress expansion even when the composite is heated.

When the content of the polyfunctional (meth)acrylate monomer is less than 2 mass %, the effect of suppressing expansion may be insufficient. When the content of the polyfunctional (meth)acrylate monomer is more than 30 mass %, the content of the monofunctional (meth)acrylate monomer is interrelatively reduced, which leads to a high probability of a temperature rise when the composite for a dental pattern resin is polymerization-cured, air bubbles mixing, and deteriorating usability. The content thereof is more preferably no more than 15 mass %.

Any polyfunctional (meth)acrylate monomer may be employed. One polyfunctional (meth)acrylate monomer may be used alone, and a plurality of polyfunctional (meth)acrylate monomers may be used in combination.

Examples of a polyfunctional (meth)acrylate monomer having two functional groups include ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, 2,2-bis[4-{3-(meth)acryloyloxy-2-hydroxypropoxy}phenyl]propane, 2,2-bis[4-(2-(meth)acryloyloxyethoxy)phenyl]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, and [2,2,4-trimethylhexamethylene bis(2-carbamoyloxyethyl)] di(meth)acrylate.

Examples of a polyfunctional (meth)acrylate monomer having at least three functional groups include trimethylolpropane tri(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexamethylene)bis[2-(aminocarboxy)propane-1,3-diol] tetramethacrylate, and 1,7-diacryloyloxy-2,2,6,6-tetraacryloyloxymethyl-4-oxyheptane.

Among them, an ethylene glycol di(meth)acrylate monomer is preferable as the polyfunctional (meth)acrylate monomer having two functional groups, and a trimethylolpropane tri(meth)acrylate monomer is preferable as the polyfunctional (meth)acrylate monomer having three functional groups. According to this, further good physical properties and usability are achieved.

Only one of the polyfunctional (meth)acrylate monomer having two functional groups and the polyfunctional (meth)acrylate monomer having three functional groups may be included, or both of them may be included. The polyfunctional (meth)acrylate monomer having three functional groups is preferably included in view of more effective achievement of the effect of suppressing expansion due to heating in burning. From such a viewpoint, the content of the polyfunctional (meth)acrylate monomer having three functional groups in all the polyfunctional (meth)acrylate monomers is preferably more than 0 mass % and no more than 20 mass %. When the content thereof is more than 20 mass %, shrinkage of the composite for a dental pattern resin when the composite is polymerization-cured tends to be too much.

<Polymerization Accelerator>

The liquid formulation in the composite for a dental pattern resin may include a polymerization accelerator. This makes it possible to further suppress expansion when the composite for a dental pattern resin is heated to be burned out, and to prevent an investment (refractory material) from being destroyed and cracking. It is imagined to be because polymerization is more certainly carried out with a polymerization accelerator, to reduce unpolymerized monomers.

A specific material as the polymerization accelerator may be suitably selected, and a tertiary amine etc. may be mainly employed. Examples of a tertiary amine include N,N'-dimethyl-p-toluidine, N,N'-dimethylaminoethyl methacrylate, triethanolamine, 4-dimethylamino methyl benzoate, 4-dimethylamino ethyl benzoate, and 4-dimethylamino isoamyl benzoate. Other examples include benzoyl peroxide, a sodium sulfinate derivative, and an organometallic compound. One of them may be used alone, or two or more of them may be used in combination.

Among them, N,N'-dimethyl-p-toluidine is preferable. This makes it possible to efficiently accelerate polymerization, and to make the above described effect greater.

The content of the polymerization accelerator in the liquid formulation in the composite for a dental pattern resin is preferably 3 mass % to 30 mass %. This makes it possible to achieve the above described effect more certainly. When the content thereof is less than 3 mass %, there is a probability of insufficiently obtaining the effect as a polymerization accelerator. When the content thereof is more than 30 mass %, storage stability tends to deteriorate.

<Others>

Other than them, a UV absorber, a coloring agent, and a polymerization inhibitor may be included as necessary. Any known ones may be employed.

[Powder Formulation]

<(Meth)Acrylate Copolymer>

The powder formulation in the composite for a dental pattern resin includes powder of a (meth)acrylate copolymer. Including more than 5 mass % of such a copolymer in all the powder formulation makes it possible to suppress shrinkage of the pattern resin in polymerization.

Specific examples of a (meth)acrylate copolymer include a copolymer of ethyl(meth)acrylate and methyl(meth)acrylate.

The composition of the (meth)acrylate copolymer is 10 mass % to 80 mass % of methyl (meth)acrylate and 20 mass % to 90 mass % of ethyl (meth)acrylate.

When the content of methyl (meth)acrylate is more than 80 mass %, the shape tends to be distorted because the composite is difficult to swell. When the content of ethyl (meth)acrylate is more than 90 mass %, too much fluidity leads to a tendency to be difficult to make a shape. More preferred composition thereof is 20 mass % to 60 mass % of methyl (meth)acrylate and is 30 mass % to 80 mass % of ethyl (meth)acrylate, and further preferred composition thereof is 20 mass % to 40 mass % of methyl (meth)acrylate and 45 mass % to 75 mass % of ethyl (meth)acrylate.

The volume median particle size (mean particle size, D50) of the (meth)acrylate copolymer is preferably 40 μm to 130 μm. Containing the (meth)acrylate copolymer having a particle size of this range makes it possible to suppress shrinkage of the composite for a dental pattern resin more certainly when the composite is polymerized, and to prevent the undesirable situations of deformation of the shape and difficult removal from a model. When the volume median particle size is less than 40 μm, the swelling rate increases, the curing time shortens, and the amount which can be taken at once with a brush-on technique reduces, which leads to a tendency of deteriorating usability. When the volume median particle size is more than 130 μm, the effect of suppressing shrinkage of the composite as described above may be little.

The volume median particle size thereof is more preferably 40 μm to 100 μm, and further preferably 40 μm to 80 μm in view of further suppressing shrinkage of the composite for a dental pattern resin when the composite is polymerization-cured.

Here, "volume median particle size", which may be also referred to as a mean particle size or D50, means a particle size when the cumulative volume index is 50%: the cumulative volume index is calculated by cumulating the volume fractions in order of a particle size from small to large. Such a volume median particle size can be measured with a laser diffraction and scattering method.

The content of the (meth)acrylate copolymer in the powder formulation in the composite for a dental pattern resin is preferably more than 5 mass % and no more than 98 mass %. This makes it possible to suppress shrinkage of the pattern more certainly when the pattern resin is polymerized. The content thereof is more preferably 20 mass % to 96 mass %, and further preferably 50 mass % to 95 mass %. This also makes it possible to improve usability.

[(Meth)Acrylate Polymer]

The powder formulation in the composite for a dental pattern resin may include powder of polymethyl (meth)acrylate that is a polymer of methyl (meth)acrylate monomers only.

The content of the powder of this polymer in all the powder formulation is preferably 5 mass % to 50 mass %. When the content is more than 50 mass %, usability may deteriorate.

Concerning the particle size of the powder of this polymer, the volume median particle size (mean particle size, D50) thereof is preferably 40 μm to 130 μm. When this particle size is more than 130 μm, the composite for a dental pattern resin when polymerization-cured tends to shrink too much.

<Flowability-Improving Agent>

Powder of a flowability-improving agent may be included in the powder formulation in the composite for a dental pattern resin. This makes it possible to prevent powder in the powder formulation from aggregating.

A material of the flowability-improving agent is not specifically restricted as long as having a function of improving flowability. Examples thereof include a polymethyl (meth)acrylate fine particle and a hydrated silicon dioxide fine particle.

Among them, a polymethyl (meth)acrylate fine particle is preferable. Using polymethyl (meth)acrylate as the flowability-improving agent makes it possible to suppress residue formation after the composite for a dental pattern resin is burned out. Residue formation indicates that the residue will muddy material for a denture base when the material for a denture base is poured into a space formed after the composite for a dental pattern resin is burned out, which will cause undesired situations.

Therefore, using polymethyl (meth)acrylate as the flowability-improving agent makes it possible to prevent not only the powder formulation from aggregating but also residue from forming after the composite for a dental pattern resin is burned out.

The volume median particle size (mean particle size, D50) of the polymethyl (meth)acrylate is preferably 0.05 μm to 20 μm, and more preferably 0.1 μm to 10 μm. When the volume median, particle size is less than 0.05 μm, the powder formulation is easy to scatter, which may lead to inconvenience on handleability. When the volume median particle size is more than 20 μm, the polymethyl (meth)acrylate absorbs the circumferences of other polymers, which may make it impossible to prevent aggregation.

The content of the polymethyl (meth)acrylate fine particles in the powder formulation is preferably 0.05 mass % to 20 mass %. When the content is less than 0.1 mass %, the effect as a flowability-improving agent is little, which may lead to deteriorating usability and storability. When the content is more than 20 mass %, the fine particles easily scatter, which may lead to deteriorating usability. The content thereof is preferably 0.05 mass % to 5 mass % specifically from the viewpoint that polymethyl (meth)acrylate fine particles of a small particle size are expensive.

<Polymerization Initiator>

The liquid formulation in the composite for a dental pattern resin may include a polymerization initiator. A polymerization initiator may be suitably selected in accordance with an aspect of polymerization of the monomers to be polymerized. As the preferred aspect, when the monofunctional (meth)acrylate monomer and the polyfunctional (meth)acrylate monomer are radical-polymerizable, such a polymerization initiator that radicals are formed may be employed.

The polymerization initiator may be suitably selected as described above. Examples thereof include acylphosphine oxides and compounds having an azide group such as camphorquinone, benzil dimethylketal, benzil diethylketal, benzil di(2-methoxyethyl) ketal, 4,4'-dimethylbenzil-dimethylketal, anthraquinone, 1-chloroanthraquinone, 2-chloroanthraquinone, 1,2-benzanthraquinone, 1-hydroxyanthraquinorte, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4'-bisdiethylaminobenzophenone, and (2,4,6-trimethylbenzoyl)diphenylphosphine oxide. One of them may be used alone, or two or more of them may be used in combination.

The content of the polymerization initiator in the liquid formulation in the composite for a dental pattern resin may be suitably adjusted as necessary, and is preferably 0.1 mass % to 5 mass %. When the content is less than 0.1 mass %, there is a probability that necessary cure cannot be carried out. When the content is more than 5 mass %, cure is too fast, which may lead to the limited operation time.

[Aspect of Composite for Dental Pattern Resin]

The liquid formulation and the powder formulation are mixed, to form the composite for a dental pattern resin.

The contents of the liquid formulation and powder formulation to be incorporated may be suitably set as necessary. The composite for a dental pattern resin is preferably constituted so as to be usable without any problem as including the liquid formulation, whose content in all the composite is within a range of 23 mass % and 43 mass %, and the powder formulation, whose content therein is within a range of 57 mass % and 77 mass %. In many cases, "liquid formulation:powder formulation=1 ml:2 g" is the standard.

The composite for a dental pattern resin as described above makes it possible to prevent its shrinkage in polymerization and expansion in heating when burned as usability for molding is kept in the process of dental precision casting including steps of molding, polymerization, and burning. Therefore, the composite for a dental pattern resin having high usability with high accuracy can be obtained.

In particular, including a polyfunctional monomer in the liquid formulation in order to prevent such expansion tends to lead to much shrinkage in polymerization. Against this, constituting the powder formulation to be applied as described above makes it possible to prevent shrinkage, and to achieve the composite for a dental pattern resin having a comprehensively high function.

Including the flowability-improving agent of polymethyl (meth)acrylate in the composite for a dental pattern resin also makes it possible to prevent residue from forming after the composite is burned out.

[Production Method]

The composite for a dental pattern resin as described above can be produced as follows, for example:

Materials of the powder formulation are weighed, and mixed and stirred using a mixer, a mortar, a bag, or the like. At this time, an organic solvent etc. may be added thereto for fixing a pigment. Water and alumina balls may be added as well for improving stirring efficiency. After stirred, the obtained powder may be put through a sieve. A step of crushing the flowability-improving agent in advance may be included.

Materials of the liquid formulation are weighed, and mixed and stirred using a mixer or the like.

EXAMPLES

Examples will be described hereinafter. The present invention is not limited to Examples.

Table 1 shows materials of the powder formulations and the liquid formulations of Examples 1 to 3 and Comparative Examples 1 to 4, and the amounts thereof. Here, each material is as follows. The units for the numerals in Table 1 are all mass %.

"(Meth)acrylate copolymer" in the powder formulation is a copolymer of ethyl methacrylate and methyl methacrylate, and the composition thereof was 70 mass % of the ethyl methacrylate and 30 mass % of the methyl methacrylate. The volume median particle size was 60 µm.

"(Meth)acrylate polymer" in the powder formulation is polymethyl methacrylate. The volume median particle size thereof was 90 µm.

"Flowability-improving agent" in the powder formulation is polymethyl methacrylate. The volume median particle size thereof was 0.5 µm.

"Monofunctional (meth)acrylate monomer" in the liquid formulation is methyl methacrylate.

"Bifunctional (meth)acrylate monomer" in the liquid formulation is ethylene glycol dimethacrylate.

"Trifunctional (meth)acrylate monomer" in the liquid formulation is trimethylolpropane trimethacrylate.

"Polymerization accelerator" in the liquid formulation is a tertiary amine, which is more specifically N,N'-dimethyl-p-toluidine.

Usability, shrinkability in polymerization, and expansibility in heating of each example were evaluated as follows:

Usability was evaluated with a brush. Specifically, a brush having immersed in the liquid formulation was dipped into the powder formulation, and a mass of the powder formulation was formed at the point of the brush. The mass was taken at mixing paper, and the following were compared with those of a conventional product (GC PATTERN RESIN by GC Corporation): the swelling rates of the powder formulation and the liquid formulation, removability from the brush when the mass was transferred from the brush to the mixing paper, and the shape of a cured product. The results are shown in such a way that when usability was better than the conventional product: good; when usability was equal to the conventional product: passed; and when usability was worse than the conventional product: failed.

Shrinkability in polymerization was evaluated by: mixing the powder formulation and the liquid formulation so that their mixing ratio was 2:1; measuring the sizes of the mixture before and after cure; and calculating the shrinkage due to the cure. The results were compared with that of a conventional product (GC PATTERN RESIN by GC Corporation). The results are shown in such a way that when the mixture did not shrink more than the conventional product: good; when the mixture shrank equally to the conventional product: passed; and when the mixture shrank more than the conventional product: failed.

Expansibility in heating was evaluated by: mixing the powder formulation and the liquid formulation so that their mixing ratio was 2:1; and shaping the mixture into a disk and curing the shaped mixture. Behaviors of the mixture expanding when the mixture was burned were shot, and compared with those of a conventional product (GC PATTERN RESIN by GC Corporation). The results are shown in such a way that when the mixture did not expand more than the conventional product: good; when the mixture expanded equally to the conventional product: passed; and when the mixture expanded more than the conventional product: failed.

Table 1 shows the results of the evaluation together with the materials of each example.

TABLE 1

| Item | Material | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|---|
| Dust formulation | (Meth)acrylate copolymer | 95 | 50 | 20 | 95 | 0 | 5 | 0 |
| | (Meth)acrylate polymer | 4 | 49 | 79 | 5 | 100 | 94 | 99 |
| | Flowability-improving agent | 1 | 1 | 1 | 0 | 0 | 1 | 1 |
| | Pigment | trace | trace | trace | trace | trace | trace | trace |
| Liquid formulation | Monofunctional (meth)acrylate monomer | 87 | 67 | 67 | 90 | 60 | 40 | 97 |
| | Bifunctional (meth)acrylate monomer | 5 | 15 | 15 | 5 | 5 | 30 | 0 |
| | Trifunctional (meth)acrylate monomer | 5 | 15 | 15 | 5 | 5 | 30 | 0 |
| | Polymerization accelerator (tertiary amine) | 3 | 3 | 3 | 0 | 30 | 3 | 3 |
| | UV absorber | trace | trace | trace | trace | trace | trace | trace |
| | Polymerization inhibitor | trace | trace | trace | trace | trace | trace | trace |
| Result | Brush (usability) | good | good | passed | passed | failed | passed | failed |
| | Shrinkability in polymerization | good | good | passed | passed | failed | failed | failed |
| | Expansibility in heating | good | good | good | passed | passed | passed | passed |

In addition to this, an example where the volume medium particle size of the (meth)acrylate copolymer in the powder formulation of Example 1 was changed to 135 μm, was tested. The other components and contents thereof were the same as in Example 1.

The results of every evaluation were "good". It is noted that shrinkability in polymerization slightly deteriorated compared to that in Example 1.

What is claimed is:

1. A composite for a dental pattern resin comprising a liquid formulation and a powder formulation, wherein
the liquid formulation comprises a polymerizable monofunctional (meth)acrylate, a polymerizable polyfunctional (meth)acrylate, and a polymerization accelerator,
the powder formulation comprises more than 5 mass % and no more than 98 mass % of a (meth)acrylate copolymer on the basis of the total powder formulation, and a flowability-improving agent, and
a volume median particle size of the (meth)acrylate copolymer is 40 μm to 130 μm, a volume median particle size of the flowability-improving agent is 0.05 μm to 20 μm, the volume median particle size of the (meth)acrylate copolymer being larger than the volume median particle size of the flowability-improving agent.

2. The composite for a dental pattern resin according to claim 1, wherein
the content of the polyfunctional (meth)acrylate is 2 mass % to 30 mass % on the basis of the total liquid formulation.

3. The composite for a dental pattern resin according to claim 1, wherein
the polyfunctional (meth)acrylate is at least one of ethylene glycol di(meth)acrylate and trimethylolpropane tri(meth)acrylate.

4. The composite for a dental pattern resin according to claim 1, wherein
the content of the polymerization accelerator is 3 mass % to 10 mass % on the basis of the total liquid formulation.

5. The composite for a dental pattern resin according to claim 1, wherein
the polymerization accelerator is N,N'-dimethyl-p-toluidine.

6. The composite for a dental pattern resin according to claim 1, wherein
the (meth)acrylate copolymer comprises ethyl (meth)acrylate and methyl (meth)acrylate.

7. The composite for a dental pattern resin according to claim 6, wherein
the content of the ethyl (meth)acrylate in the (meth)acrylate copolymer is 20 mass % to 90 mass %, and the content of the methyl (meth)acrylate in the (meth)acrylate copolymer is 10 mass % to 80 mass %.

8. The composite for a dental pattern resin according to claim 1, wherein
the content of the flowability-improving agent is 0.1 mass % to 20 mass % on the basis of the total powder formulation.

9. The composite for a dental pattern resin according to claim 1, wherein the flowability-improving agent is polymethyl (meth)acrylate.

10. A composite for a dental pattern resin comprising a liquid formulation and a powder formulation, wherein
the liquid formulation comprises a polymerizable monofunctional (meth)acrylate, a polymerizable polyfunctional (meth)acrylate, and a polymerization accelerator,
the powder formulation comprises 50 mass % to 95 mass % of a (meth)acrylate copolymer on the basis of the total powder formulation, and a flowability-improving agent, and
a volume median particle size of the (meth)acrylate copolymer is 40 μm to 130 μm, a volume median particle size of the flowability-improving agent is 0.05 μm to 20 μm, the volume median particle size of the (meth)acrylate copolymer being larger than the volume median particle size of the flowability-improving agent.

* * * * *